United States Patent [19]

Suzuki et al.

[11] Patent Number: 5,320,776

[45] Date of Patent: Jun. 14, 1994

[54] ANTIFERROELECTRIC LIQUID CRYSTAL COMPOUND

[75] Inventors: Yoshiichi Suzuki, Tokyo; Toru Ohde, Tokyo, both of Japan

[73] Assignee: Showa Shell Sekiyu Kabushiki Kaisha, Tokyo, Japan

[21] Appl. No.: 63,570

[22] Filed: May 19, 1993

[30] Foreign Application Priority Data

May 20, 1992 [JP] Japan ................................ 4-152886
Sep. 29, 1992 [JP] Japan ................................ 4-283949

[51] Int. Cl.$^5$ ...................... C09K 19/22; C09K 19/20; C09K 19/12; C07C 235/44
[52] U.S. Cl. ........................ 252/299.68; 252/299.01; 252/299.64; 252/299.65; 252/299.66; 252/299.67; 564/161
[58] Field of Search ............... 252/299.01, 299.64, 252/299.65, 299.66, 299.67, 299.68; 564/161

[56] References Cited

U.S. PATENT DOCUMENTS

| | | | |
|---|---|---|---|
| 4,921,632 | 5/1990 | Nakamura et al. | 252/299.01 |
| 5,108,650 | 4/1992 | Koden et al. | 252/299.01 |
| 5,207,947 | 5/1993 | Suzuki et al. | 252/299.67 |

FOREIGN PATENT DOCUMENTS 0422996 4/1991 European Pat. Off. .

62-283955 12/1987 Japan .

OTHER PUBLICATIONS

Patent Abstracts of Japan, vol. 12, No. 176, May 25, 1988 and JPA 62-283 955 (Toray Ind.) Dec. 1987.

*Primary Examiner*—Shean Wu
*Attorney, Agent, or Firm*—Cushman, Darby Cushman

[57] ABSTRACT

A novel antiferroelectric liquid crystal compound is disclosed which is represented by the following formula:

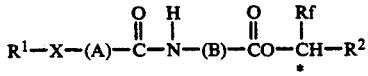

wherein $R^1$ and $R^2$ are independently selected from $C_3$–$C_{18}$ alkyl groups, respectively, Rf is a lower fluoroalkyl group, X is a group selected from the group consisting of —O—, —COO—, —OOC—, and —CO—, or a single bond, (A) and (B) each is independently a group selected from the group consisting of phenyl, biphenyl, and naphthalene group which may be substituted with a halogen atom, and C having an asterisk indicates an asymmetric carbon atom.

6 Claims, 4 Drawing Sheets

APPLIED TRIANGULAR WAVE VOLTAGE

OPTICAL RESPONSE OF NEMATIC LIQUID CRYSTAL ON MARKET

OPTICAL RESPONSE OF LIQUID CRYSTAL HAVING IDEAL BISTABLE STATES

OPTICAL RESPONSE OF LIQUID CRYSTAL HAVING TRISTABLE STATES OF PRESENT INVENTION

SWITCHING OF BISTABLE STATES

SWITCHING OF TRISTABLE STATES

ANTIFERROELECTRIC LIQUID CRYSTAL COMPOUND

FIELD OF THE INVENTION

The present invention relates to a novel liquid crystal compound having an amide linkage.

The optically active liquid crystal compound of the present invention has a ferroelectric property showing bistable states and, also, has an antiferroelectric property showing tristable states. The liquid crystal compound is used for display elements and electrooptical devices utilizing the response to the changes in an electric, field.

BACKGROUND OF THE INVENTION

As elooptical apparatuses using a liquid crystal, electrooptical apparatuses using nematic liquid crystals such as a DSM type display, TN type display, G-H type display, or STN type display have been developed and practically used. However, all of the electrooptical apparatuses nematic liquid crystals suffer the drawback response time is as slow as several msec to several tens msec, which results in a limited range of applications. The flow response of the electrooptical apparatuses or elements using nematic liquid crystals is due to the fact that the torque which changes the direction of molecules is inherently based on the anisotropy of dielectric constant and thus, the force is not so strong. With such a technical background, the development of a ferroelectric liquid crystal had been attempted which has a spontaneous polarization (Ps), has a strong torque based on $Ps \times E$ (E is an applied voltage), and has an extremely short optical response time of few $\mu$sec to several tens $\mu$sec to make the preparation of a ultrahigh speed device possible.

Mayer et al. synthesized DOBAMBC (p-decyloxybenzilidene-p-ammino-2-methylbutyl cinnamate) in 1975 for the first time in the world and which was confirmed to be a ferroelectric liquid crystal (Le Journal de Physique, Vol. 36, 1975, L-69).

Further, since Clark and Lagerwall reported in 1980 on such characteristics on display devices as high velocity response of submicroseconds and memory characteristics of DOBAMC, ferroelectric liquid crystals have drawn considerable public attention (N.A. Clark et al., Appl. Phys. Lett. 36, 899 (1980)).

However, many technical problems in the above mentioned system have presented obstacles to its practical application. In particular, no material was reported as exhibiting ferroelectric liquid crystallinity at an ambient temperature. Moreover, an effective and practical method was not established to control the molecular alignment of the liquid crystal molecules. Control of the molecular alignment is essential in order to have an effective and practical liquid crystal display device.

After the publication of the report, various attempts have been made from both aspects of liquid crystal materials and device, display devices utilizing the switching between twisted bistable states were prepared for trial, and high speed electrooptical apparatuses using the device are proposed in U.S. Pat. No. 4,367,924 and others. However, high contrast and proper potential of threshold value have not been obtained.

From such a point of view, other switching systems were explored to propose a transitional diffusion system. Subsequently, a three states switching system of liquid crystal having tristable states was reported in 1988 (A. D. L. Chandani, T. Hagiwara, Y. Suzuki et al., Japan, J. of Appl. Phys., 27, (5), L729-L732 (1988)).

The optically tristable states herein referred to mean that, when voltage in the form of a triangular wave as in FIG. 1 A is applied to liquid crystal electrooptical devices where antiferroelectric liquid crystals are laid between the first electrode substrate plate and the second electrode substrate plate which is apart at a given space from the first one, the antiferroelectric liquid crystal shows the first stable molecular orientation and resulting the first optically stable state shown in FIG. 3 (a), and FIG. 1(D) at point 2, respectively, when electric voltage is zero. The antiferroelectric liquid crystal shows the second stable molecular orientation and resulting the second optically stable state shown in FIG. 3 (b), and FIG. 1(D) at point 1, respectively, in one of the direction of electric field and shows the third stable molecular orientation and resulting the third optically stable state shown in FIG. 3 (c), and FIG. 1(D) at point 3, in the other direction of electric field.

Liquid crystal electrooptical apparatuses utilizing the tristable states, that is three states, are proposed in U.S. Pat. No. 5,046,823 filed by the present applicant.

The characteristics of an antiferroelectric liquid crystal showing the tristable states are described in more detail below.

In the ferroelectric liquid crystal element having a stabilized surface which was proposed by Clark-Lagerwall, ferroelectric liquid crystal molecules show two stable states in which the molecules are uniformly oriented or aligned in one direction in the phase S*C. The molecules are stabilized in either state depending on the direction of applied electric field as shown in FIG. 2 at point (a) and at point (b), and the state is kept even when the field was shut off.

Actually, however, the alignment of the ferroelectric liquid crystal molecules shows twisted two states in which directors of the liquid crystal molecules are twisted or shows a chevron structure in which layers are bent in a doglegged shape. In the chevron layer structure, switching angle becomes small, forming a cause for a low contrast, and which constitute a serious obstacle for its practical use.

On the other hand, in the liquid crystal electrooptical devices, an "anti" ferroelectric liquid crystal molecules are aligned in antiparallel, tilting in opposite direction at every adjoining layer, in the phase S*(3) showing the tristable states, and thus, the dipoles of the liquid crystal molecules are negating each other. Accordinqly, the spontaneous polarization is nullified as a whole. The transmittance of the liquid crystal phase showing such molecular alignment corresponds to point 2 in FIG. 1 D.

Further, when a voltage sufficiently higher than a threshold value of (+) or (−) was applied, liquid crystal molecules shown in FIG. 3 (b) or (c) are tilted in the same direction and aligned in parallel. In this state, the spontaneous polarization is produced since the dipoles are also shifted to the same direction to form a ferroelectric phase, and the transmittance of the liquid crystal phase in that state corresponds to points 1 and 3 in FIG. 1 D.

That is, in the phase S*(3) of the "anti" ferroelectric phase, the "anti" ferroelectric phase at the time of no-electric field and two ferroelectric phases due to the polarity of applied electric field are stabilized, and switching is carried out among tristable states of an "anti" ferroelectric phase and two ferroelectric phases, with a direct current-like threshold value. Based on the change in the alignment of liquid crystal molecules accompanied with the switching, light transmittance is changed while drawing such a double hysteresis as shown in FIG. 4.

One of the characteristics of the present invention is that a memory effect can be realized by applying a bias voltage to the double hysteresis as shown in FIG. 4 (A) and then, further applying a pulse voltage.

Moreover, the ferroelectric phase is stretched in terms of its layer by the application of an electric field to form a book-shelf structure. On the other hand, in the "anti" ferroelectric phase of the third stable state, an analogous book-shelf structure is formed. Since the layer structure switching due to the application of an electric field gives a dynamic shear to liquid crystal layers, an alignment defect is improved during driving, and thus, a good molecular alignment can be realized.

In the "anti" ferroelectric liquid crystal, since image display is performed by alternatively using both hysteresises of plus side and minus side, afterimage phenomenon due to the accumulation of inner electric field based on the spontaneous polarization can be prevented.

As explained above, the "anti" ferroelectric liquid crystal can be said to be a very useful liquid crystal compound having advantages as follows:

1) Ultrahigh speed response is possible,
2) High contrast and wide viewing angle can be expected, and
3) Excellent alignment characteristics and memory effect can be realized.

Reports are made on the liquid crystal phase of the "anti" ferroelectric liquid crystal showing the tristable states in the following articles:

1) A. D. L. Chandani et al., Japanese J. Appl. Phys., 28, L-1265 (1989), and
2) H. Orihara et al., Japanese J. Appl. Phys., 29, L-333 (1990).

The liquid crystal phase is called "Phase $S^*_{CA}$" (Antiferroelectric Smectic C phase) in association with the "anti" ferroelectric property. The phase is named "phase $S^*_{(3)}$" in the present specification since the liquid crystal phase performs the switching among tristable states.

The liquid crystal compounds which have the "anti" ferroelectric phase $S^*(3)$ showing the tristable states in a phase series are disclosed in Japanese Unexamined Patent Publication No. 1-316367, U.S. Pat. Nos. 5,171,471 and 4,973,738, and European Patent No. 330,491 A filed by the present inventions, and in Japanese Unexamined Patent Publication No. 1-213390 filed by Ichihashi et al. Liquid crystal electrooptical devices utilizing the tristable states are proposed in Japanese Unexamined Patent Publication No. 2-2-40625 and U.S. Pat. No. 5,046,823.

The liquid crystal compounds having an amide linkage are reported in Japanese Unexamined Patent Publication Nos. 63-126865, 63-132869, and 2-151684.

However, Japanese Unexamined Patent Publication No. 63-126865 has disclosed optically active, cyclic amide compounds such as indole ring compounds, and Japanese Unexamined Patent Publication No. 63-132869 has disclosed compounds prepared by using L-isoleucine derived from a natural substance as a starting raw material. Both of them are chiral dopane compounds producing a ferroelectric chiral smectic base liquid crystal.

Further, Japanese unexamined Patent Publication No. 2-151684 has produced the use of amides such as dimethyl formamide, dibutyl formamide, and diphenyl formamide as a stabilizer to a change with the passage of time of a liquid crystal phase.

As will be understood from the above, a report has not yet been published on an "anti" ferroelectric liquid crystal having an amide linkage.

SUMMARY AND OBJECTS OF THE INVENTION

A novel antiferroelectric liquid crystal compound according to the present invention is represented by the following formula:

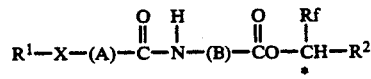

wherein $R^1$ and $R^2$ are independently selected from $C_3$-$C_{18}$ alkyl groups, respectively, Rf is a lower fluroalkyl group, X is a group selected form the group consisting of —O—, —COO—, —OOC—, and —CO—, or a single bond, (A) and (B) are each independently selected from the group consisting of 1,4, phenylene, biphenylene and naphthalene which may be substituted with a halogen atom, and the C having an asterisk indicates an asymmetric carbon atom.

An object of the present invention is to provide a novel antiferroelectric liquid crystal compound having an amido bond.

An object of the present invention is to provide a novel antiferroelectric liquid crystal compound which is useful for display elements in electrooptical devices.

DETAILED DESCRIPTION OF THE INVENTION

Figure 1A:
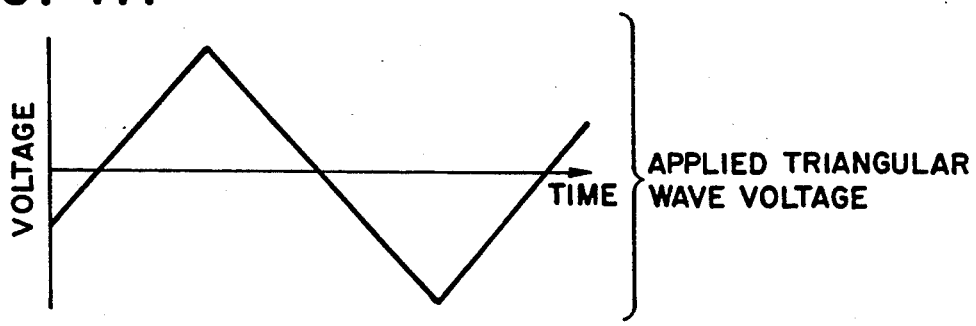
FIG. 1(A) shows an applied triangular wave.
Figure 1B:
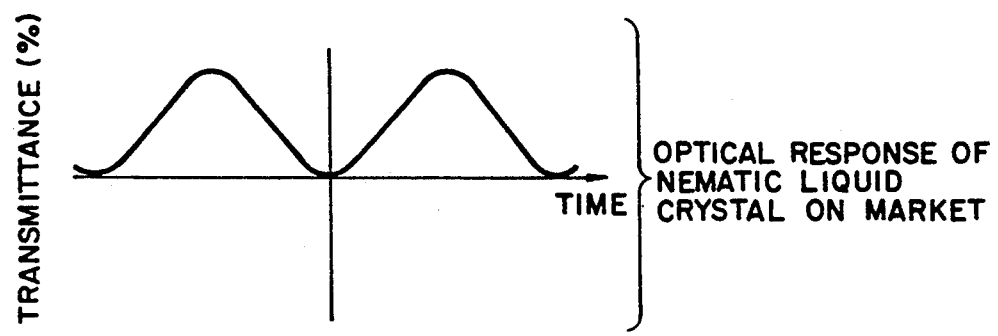
FIG. 1(B), FIG. 1(C) and FIG. 1(D) show optical response characteristics of a commercially available nematic liquid crystal, of a liquid crystal exhibiting bistable states, and of a liquid crystal showing tristable states, respectively.
Figure 1C:
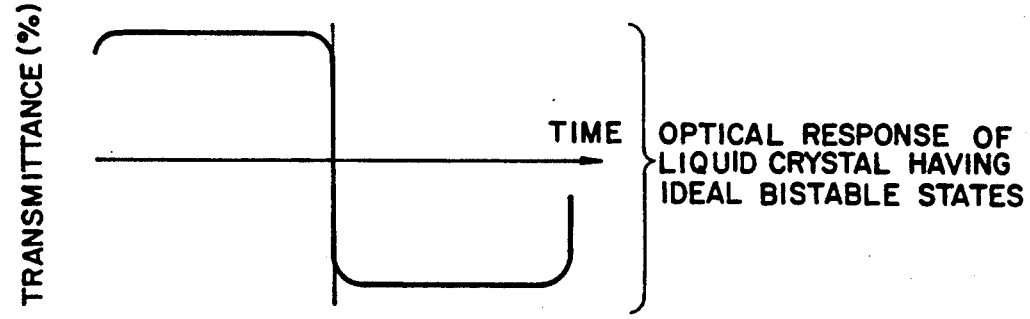
Figure 1D:
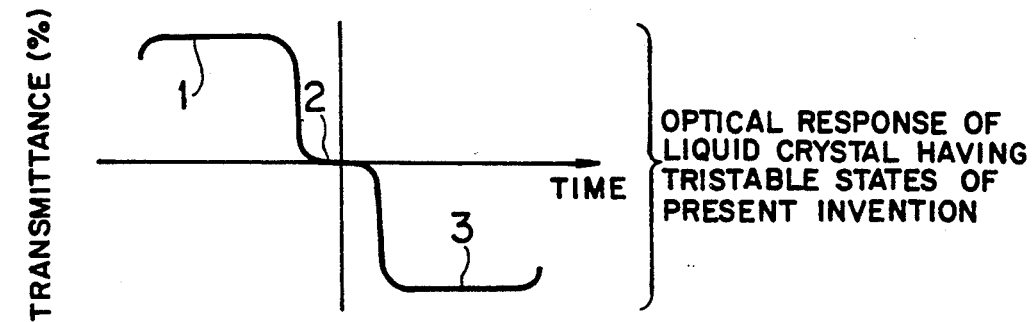
Figure 2:
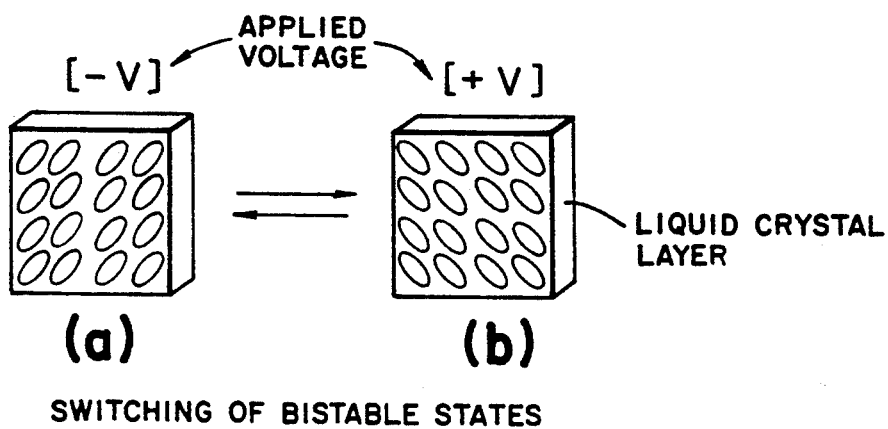
FIG. 2 shows the appearance of aligned ferroelectric liquid crystal molecules in two stabilized states, designated by reference letters (a) and (b), as proposed by Clark and Lagerawll.
Figure 3:
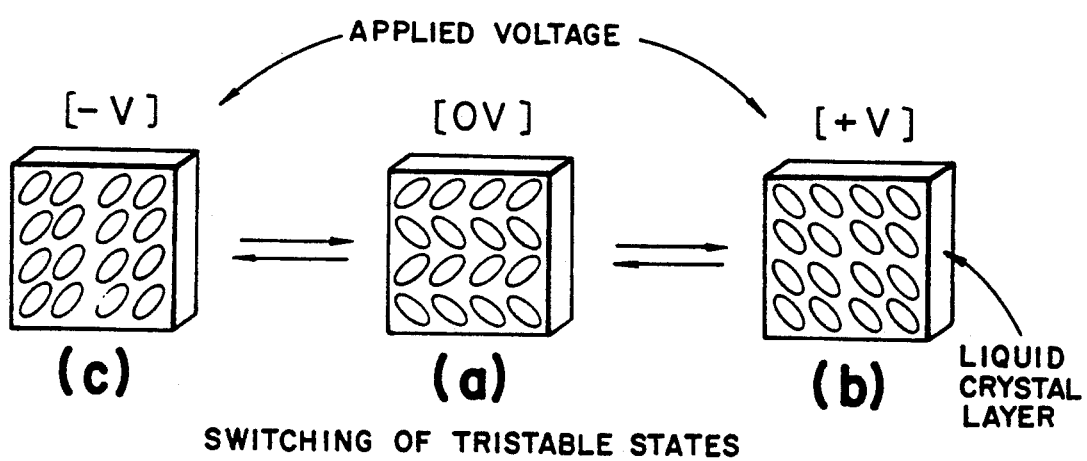
FIG. 3 shows the appearance of aligned "anti" ferroelectric liquid crystal molecules of the present invention in three different stable states, which states are designated by the reference letters (a), (b) and (c).
Figure 4:
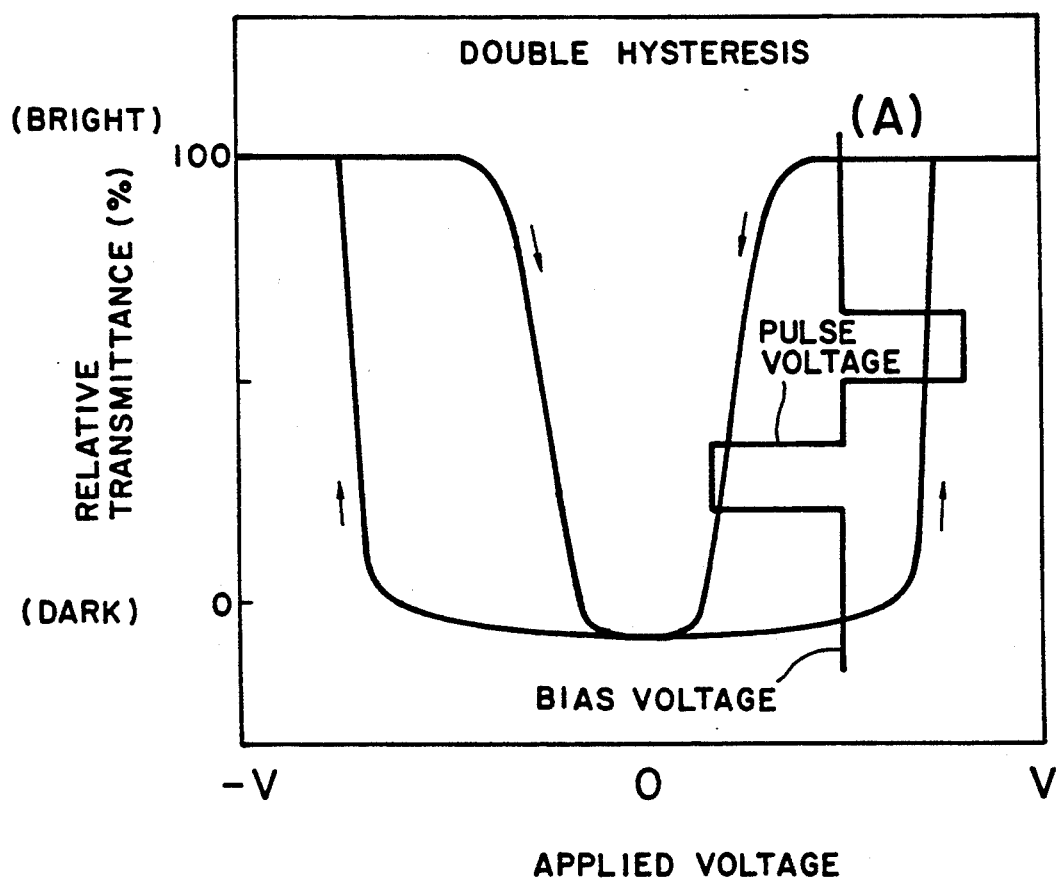
FIG. 4 is a graph showing characteristics of applied voltage-light transmittance indicating that antiferroelectric liquid crystal molecules change their light transmittance while drawing double hysteresis curves following the applied voltage. Reference point (A) in FIG. 4 refers to application of a bias voltage to the double hysteresis and further applying a pulse voltage.

The present invention relates to an antiferroelectric liquid crystal compound represented by the following formula:

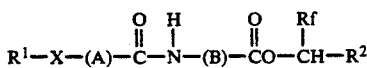

wherein $R^1$ and $R^2$ are independently selected from $C_3$-$C_{18}$ alkyl groups, respectively, Rf is a lower fluoroalkyl, group, X is a group selected from the group consisting of —O—, —COO—, —OOC—, and —CO—, or a single bond, each of the (A) and (B) is a group independently selected from the group consisting of phenyl, biphenyl, and naphthalene group which may be substituted with a halogen atom, and C having an asterisk indicates an asymmetric carbon atom.

It is preferable in the present invention that each of the (A) and (B) in the general formula mentioned above is a group independently selected from the group consisting of

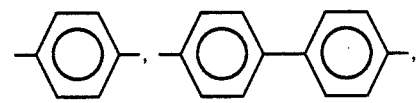

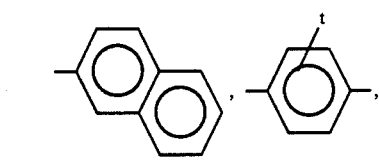

wherein t represents a halogen atom and Rf is a group selected from the group consisting of $CF_3$, $C_2F_5$, $CHF_2$, and $CH_2F$.

Further, it is more preferable in the present invention that the (A) is

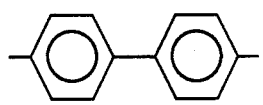

group and (B) is

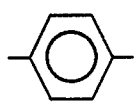

group.

Also, the X mentioned above is preferably —COO— group.

Examples of the general methods for synthesizing the compounds of the present invention are explained as follows:

Case 1:

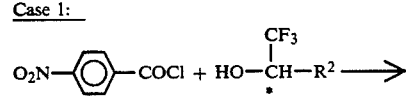

-continued

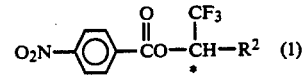 (1)

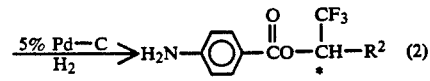 (2)

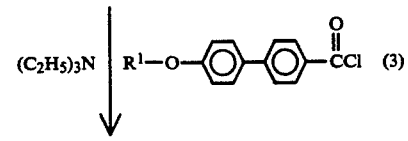 (3)

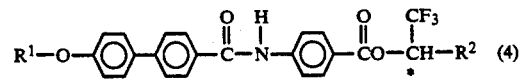 (4)

Case 2:

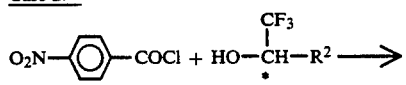

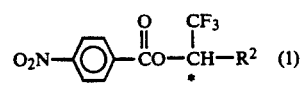 (1)

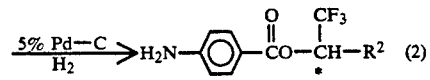 (2)

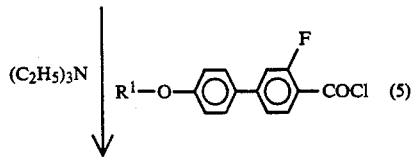 (5)

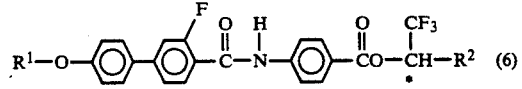 (6)

Case 3:

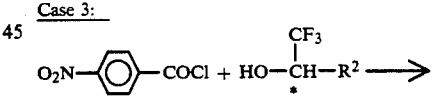

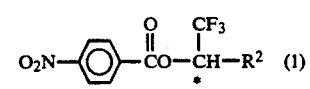 (1)

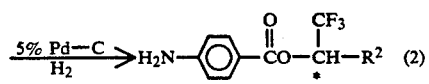 (2)

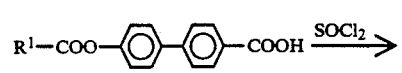

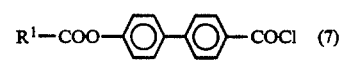 (7)

(2) + (7) ⟶

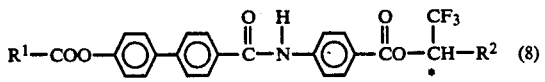 (8)

In the methods for producing the compounds of the present invention, p-nitrobenzoyl chloride is first reacted with optically active 1,1,1-trifluoro-2-alkanol to form 1,1,1-trifluoro-2-alkyl p-nitrobenzoate (1). Then, the nitro group in the ester (1) is converted into amino group in the compound (2). The catalyst used in this process is preferably palladium-carbon catalyst, $PtO_2$-$RhO_2$ catalyst, Raney nickel catalyst, or $CuCr_2O_4$ catalyst under hydrogen atmosphere. However, zinc-hydrochloric acid or stannous chloride-hydrochloric acid catalyst may also be used for converting the nitro group into the amino group.

By the reaction of the compound (2) with 4-alkyloxybiphenyl-4'-carboxylic acid chloride (3) or 4-alkyloxy-3'-fluorobiphenyl-4'-carboxylic acid chloride (5), the compound (4) or (6) which is the purpose of the present invention can be produced.

Also, 4'-alkylcarbonyloxybiphenyl-4-carboxylic acid chloride (7) can be used, instead of the compound (3) or (5), to produce the objective compound (8).

According to the present invention, a novel antiferroelectric liquid crystal compound having an amide linkage can be provided for the first time.

EXAMPLE

The present invention will now be described in further detail with reference to Examples. However, it should be understood that the present invention is by no means restricted by such specific Examples.

EXAMPLE 1

[1]Synthesis of
N-4-(1,1,1-trifluoro-2-octyloxycarbonyl)phenyl
4'-n-octyloxybiphenyl-4-carboxamide

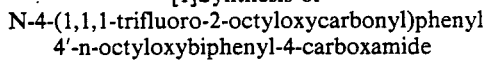

Synthesis of 1,1,1-trifluoro-2-octyl p-aminobenzoate

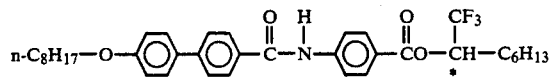

To 50 ml of methylene chloride which was mixed with 2 g of (R)-(−)-1,1,1-trifluoro-2-octanol $[\alpha]D^2 = \pm 25.59$ (measured in $CHCl_3$ at a concentration of 0.9951 % by weight) and 1.15 g of triethyl amine, was slowly added dropwise 50 ml of methylene chloride solution of 2.4 g of p-nitrobenzoyl chloride, with stirring at a temperature of 0° C., then a catalytic amount of dimethylamino pyridine was further added. The solution was subjected to reaction overnight at an ambient temperature.

The reaction liquid was poured into water, and extracted with methylene chloride, then, the organic layer was washed with a diluted hydrochloric acid and water in this order. The organic layer thus recovered was distilled under a reduced pressure to remove the solvent, and subjected to purification by a silica gel chromatography (n-hexane:ethyl acetate=10:2) to obtain 1.9 g of 1,1,1-trifluoro-2-octyl p-nitrobenzoate. The ester was dissolved in 30 ml of ethanol, to which 0.19 g of 5 % Pd-C catalyst was added. After the solution was stirred overnight under hydrogen atmosphere, the Pd-C catalyst was separated by filtration, and then the ethanol was distilled off under a reduced pressure to obtain 1.8 g of 1,1,1-trifluoro-2-octyl p-aminobenzoate which was the desired compound of the reaction [1].

Synthesis of
N-4-(1,1,1-trifluoro-2-octyloxycarbonyl)phenyl
4'-n-octyloxybiphenyl-4-carboxamide

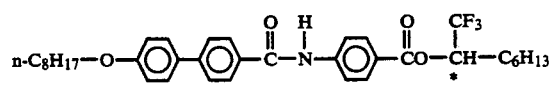

After 1.2 g of 4'-n-octyloxybiphenyl-4-carboxylic acid was heated together with an excess amount of thionyl chloride for 6 hours under reflux condition, unaltered thionyl chloride was distilled off to obtain 1.25 g of 4-n-octyloxybiphenylcarboxylic acid chloride.

Then, 1 g of the 1,1,1-trifluoro-2-octyl p-aminobenzoate obtained in [1]above, 0.35 g of triethyl amine, and 0.13 g of dimethylamino pyridine were dissolved in 30 ml of methylene chloride. To the solution, was slowly added 30 ml of methylene chloride in which 0.25 g of the 4-n-octyloxybiphenyl carboxylic acid chloride synthesized in the process mentioned above was dissolved dropwise while being cooled with ice, and the solution was stirred for a whole day and night at an ambient temperature.

The reaction mixture was put in water, and subjected to repeated extraction with methylene chloride. The methylene chloride layer was washed with a diluted hydrochloric acid and water in this order, then dried over anhydrous magnesium sulfate, and distilled to remove the solvent, and the residue was purified by a silica gel chromatography and recrystallized to obtain 0.52 g of N-4-(1,1,1-trifluoro-2-octyloxycarbonyl)phenyl 4'-n- octyloxybiphenyl-4-carboxamide.

The phase transition temperatures (° C.) observed with a microscope equipped with a hot stage were as follows:

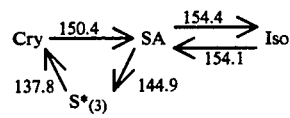

EXAMPLE 2

Synthesis of
N-1-(1,1,1-trifluoro-2-octyloxycarbonyl)phenyl
4'-n-nonyloxybiphenyl-4-carboxamide

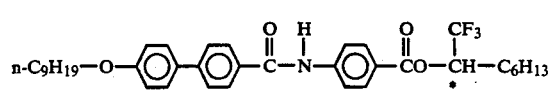

Example 1 was repeated except that 1.2 g of 4'-nonyloxybiphenyl-4-carboxylic acid was used instead of 4'-n-octyloxybiphenyl-4-carboxylic acid used in the reaction [2] in Example 1 to obtain the titled compound.

The phase transition temperatures (° C.) observed with a microscope equipped with a hot stage were as follows:

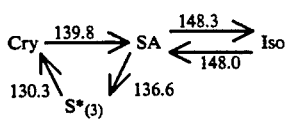

EXAMPLE 3

Synthesis of
N-4-(1,1,1-trifluoro-2-octyloxycarbonyl)phenyl
4'-n-decyloxybiphenyl-4-carboxamide

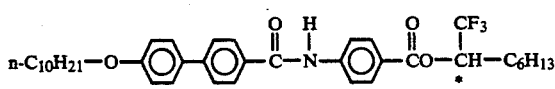

Example 1 was repeated except that 1.4 g of 4'-n-decyloxybiphenyl-4-carboxylic acid was used instead of 4'-n-octyloxybiphenyl-4-carboxylic acid used in the reaction [2] in Example 1 to obtain the titled compound.

The phase transition temperatures (° C.) observed with a microscope equipped with a hot stage were as follows:

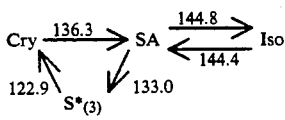

EXAMPLE 4

Synthesis of
N-4-(1,1,1-trifluoro-2-octyloxycarbonyl)-phenyl
4'-n-dodecyloxybiphenyl-4-carboxamide

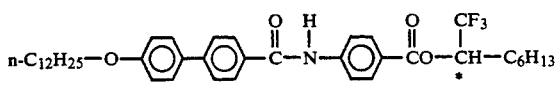

Example 1 was repeated except that 1.6 g of 4'-n-dodecyloxybiphenyl-4-carboxylic acid was used instead of 4'-n-octyloxybiphenyl-4-carboxylic acid used in the reaction [2] in Example 1 to obtain the titled compound. The phase transition temperatures (° C.) observed with a microscope equipped with a hot stage were as follows:

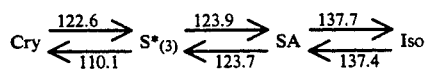

EXAMPLE 5

Synthesis of
N-4-(1,1,1-trifluoro-2-decyloxycarbonyl)phenyl
4'-n-nonyloxybiphenyl-4-carboxamide

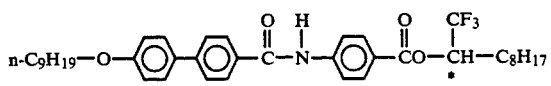

[1] Synthesis of p-aminobenzoic acid
1,1,1-trifluoro-2-decyl ester

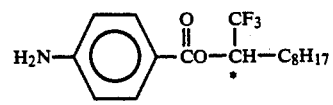

To 50 ml of methylene chloride mixed with 2.3 g of (R)-(−)-1,1,1-trifluoro-2-decanol [α] $D^{20}$=+23.10 (measured in CHC13 at a concentration of 0.9453 % by weight) and 1.15 g of triethyl amine, was slowly added 50 ml of methylene chloride solution of 2.4 g of p-nitrobenzoic acid chloride dropwise with stirring at a temperature of 0° C., then a catalytic amount of dimethylamino pyridine was further added, and the solution was subjected to reaction overnight at an ambient temperature.

The reaction liquid was poured into water, and extracted with methylene chloride. The methylene chloride layer was washed with a diluted hydrochloric acid and water in this order. The organic layer thus recovered was distilled under a reduced pressure to remove the solvent, and subjected to purification by a silica gel chromatography (n-hexane:ethyl acetate=10:2) to obtain 2.1 g of p-nitrobenzoic acid 1,1,1-trifluoro-2-decyl ester. The ester was dissolved in 30 ml of ethanol, to which 0.21 g of 5 % Pd-C catalyst was added, and the solution was stirred overnight under hydrogen atmosphere, then the Pd-C catalyst was separated by filtration, and the ethanol was distilled off under a reduced pressure to obtain 2.0 g of p-amino-benzoic acid 1,1,1-trifluoro-2-decyl ester which was the desired compound of the reaction [1].

[2]Synthesis of
N-4-(1,1,1-trifluoro-2-decyloxycarbonyl)phenyl
4'-n-nonyloxybiphenyl-4-carboxamide

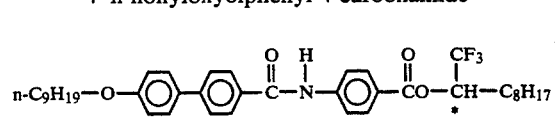

After 1.2 g of 4'-n-nonyloxybiphenyl-4-carboxylic acid was heated together with an excess amount of thionyl chloride for 6 hours under a reflux condition, unaltered thionyl chloride was distilled off to obtain 1.25 g of 4'-n-nonyloxybiphenyl-4-carboxylic acid chloride.

Next, 1.1 g of the p-aminobenzoic acid 1,1,1-trifluoro-2-decyl ester, 0.35 g of triethyl amine, and 0.13 g of dimethylamino pyridine were dissolved in 30 ml of methylene chloride. To the solution was slowly added 30 ml of methylene chloride in which 1.25 g of the 4'-n-nonyloxybiphenyl-4-carboxylic acid chloride which was synthesized by the process mentioned above was dissolved dropwise while being cooled with ice, and the solution was stirred for a whole day and night at an ambient temperature.

The reaction mixture was put into water, and subjected to repeated extraction with methylene chloride, then the methylene chloride layer was washed with a diluted hydrochloric acid and water in this order, then dried over anhydrous magnesium sulfate and distilled to remove the solvent, and then the residue was purified by a silica gel chromatography and recrystallized to obtain 0.6 g of N-4-(1,1,1-trifluoro-2-decyloxycarbonyl)phenyl 4'-n-carboxamide. nonyloxybiphenyl-4-carboxamide.

The phase transition temperatures (° C.) observed with a microscope equipped with a hot stage were as follows:

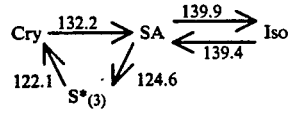

EXAMPLE 6

Synthesis of N-4-(1,1,1-trifluoro-2-decyloxycarbonyl)phenyl 4'-n-decyloxybiphenyl-4-carboxamide

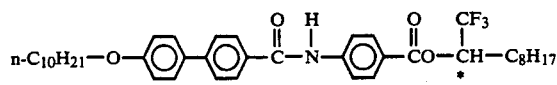

Example 5 was repeated except that 1.3 g of 4'-n-decyloxybiphenyl-4-carboxylic acid was used instead of 4'-n-nonyloxybiphenyl-4-carboxylic acid used in the reaction [2] in Example 5 to obtain the desired compound.

The phase transition temperatures (° C.) observed with a microscope equipped with a hot stage were as follows:

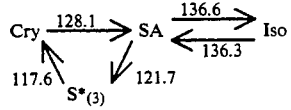

EXAMPLE 7

Synthesis of N-4-(1,1,1-trifluoro-2-decyloxycarbonyl)-phenyl 4'-n-dodecycloxybiphenyl-4-carboxamide

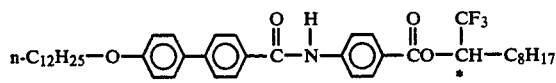

Example 5 was repeated except that 4'-n-dodecycloxybiphenyl-4-carboxylic acid was used instead of 4'-n-nonyloxybiphenyl-4-carboxylic acid used in the reaction [2] in Example 5 to obtain the titled compound.

The phase transition temperatures (° C.) observed with a microscope equipped with a hot stage were as follows:

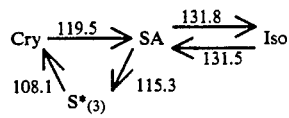

EXAMPLE 8

Synthesis of N-4-(1,1,1-trifluoro-2-octyloxycarbonyl)-phenyl 4'-n-nonanoyloxybiphenyl-4-carboxamide

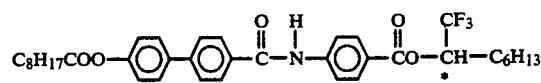

1) Synthesis of 1,1,1-trifluoro-2-octyl amino benzoate

To 50 ml of methylene chloride which was mixed with 2 g of (R)-(−)-1,1,1-trifluoro-2-octanol $[\alpha]_D^{20} = \pm 25.59$ (measured in CHCl$_3$ at a concentration of 0.9951% by weight) and 1.15 g of triethyl amine, was slowly added 50 ml of methylene chloride solution of 2.4 g of p-nitrobenzoyl chloride dropwise with stirring at a temperature of 0° C., then a catalytic amount of dimethylamino pyridine was further added, and the solution was subjected to reaction overnight at an ambient temperature.

The reaction liquid was poured into water, and extracted with methylene chloride. The methylene chloride layer was washed with a diluted hydrochloric acid and water in this order. The organic layer thus recovered was distilled under a reduced pressure to remove the solvent, and subjected to purification by a silica gel chromatography (n-hexane:ethyl acetate=10:2) to obtain 1.9 g of p-nitrobenzoic acid 1,1,1-trifluoro-2-octyl ester. The ester was dissolved in 30 ml of ethanol, to which 0.19 g of 5% Pd-C catalyst was added. After the solution was stirred overnight under hydrogen atmosphere, the Pd-C catalyst was separated by filtration, and the ethanol was distilled off under a reduced pressure to obtain 1.8 g of p-aminobenzoic acid 1,1,1-trifluoro-2-octyl ester which was the desired compound of the reaction 1).

2) Synthesis of 4'-n-nonanoyloxybiphenyl-4-carboxylic acid

To 13 ml of methylene chloride, were dissolved 1.25 g of 4'-hydroxybiphenyl-4-carboxylic acid and 0.52 g of triethyl amine. To the solution was added 10 ml of methylene chloride solution of 1.2 g of nonanoyl chloride dropwise with stirring at an ambient temperature. Further, 0.2 g of dimethylamino pyridine was added and the solution was stirred for a whole day and night at an ambient temperature. After the termination of the reaction, the solution was concentrated under a reduced pressure, the reaction liquid was poured into water and neutralized, and the precipitate thus formed was separated by filtration, and washed with hexane, and dried under a reduced pressure to obtain 1.72 g of the desired compound.

3) Synthesis of 4'-n-nonanoyloxybiphenyl-4-carboxylic acid chloride

To 5 ml of thionyl chloride, was dissolved 1.72 g of 4'-n-nonanoyloxybiphenyl-4-carboxylic acid chloride. Further a few drops of N,N-dimethyl formamide were added, and the solution was heated to reflux for 10 hours. After the termination of the reaction, an unaltered thionyl chloride was distilled off under a reduced pressure to obtain 1.81 g of the desired compound.

4) Synthesis of N-4-(1,1,1-trifluoro-2-octyloxycarbonyl)phenyl 4'-n-nonanoyloxybiphenyl-4-carboxamide To 5 ml of methylene chloride solution of 0.25 g of 1,1,1-trifluoro-2-octyl 4-aminobenzoate and 0.10 g of triethyl amine, was added 5 ml of methylene chloride solution of 0.37 g of 4'-n-nonanoyloxybiphenyl-4-carboxylic acid chloride dropwise with stirring. Further, 0.03 g of dimethylamino pyridine was added and the solution was stirred for a whole day and night at an ambient temperature. After the termination of the reaction, the solution was poured into water and neutralized, and the methylene chloride layer was separated and dried over anhydrous magnesium sulfate. The solvent was distilled off under a reduced pressure, then the crude product thus obtained was purified by a silica gel chromatography using the same solvent as used in Example 1, and further subjected to recrystallization to obtain 0.20 g of the desired compound.

The phase transition temperatures (° C) observed with a microscope equipped with a hot stage were as follows:

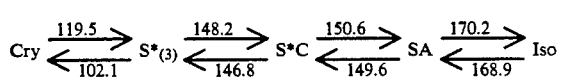

EXAMPLE 9
Synthesis of N-4-(1,1,1-trifluoro-2-octyloxycarbonyl)phenyl 4'-n-decanoyloxybiphenyl-4-carboxamide

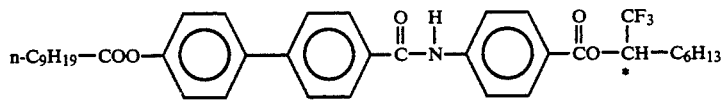

Example 8 was repeated except that 1.4 g of n-decanoic acid chloride was used instead of n-nonanoyl chloride used in the reaction 2) in Example 8 to obtain the titled compound.

The phase transition temperatures (° C.) observed with a microscope equipped with a hot stage were as follows:

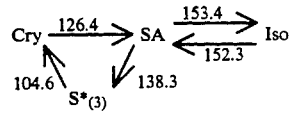

EXAMPLE 10
Synthesis of N-4-(1,1,1-trifluoro-2-octyloxycarbonyl)phenyl 4'-n-undecanoyloxybiphenyl-4-carboxamide

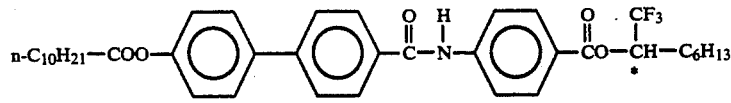

Example 8 was repeated except that 1.5 g of n-undecanoic acid chloride was used instead of n-nonanoyl chloride used in the reaction 2) in Example 8 to obtain 0.10 g of the titled compound.

The phase transition temperatures (° C.) observed with a microscope equipped with a hot stage were as follows:

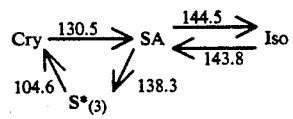

EXAMPLE 11
Synthesis of N-4-(1,1,1-trifuloro-2-octyloxycarbonyl)phenyl 4'-n-dodecanoyloxybiphenyl-4-carboxamide

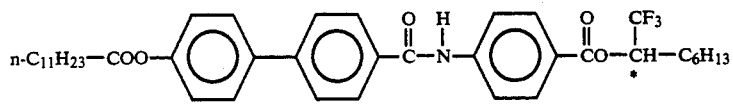

Example 8 was repeated except that 1.6 g of n-dodecanoic acid chloride was used instead of n-nonanoic acid chloride used in the reaction 2) in Example 8 to obtain 0.12 g of the titled compound.

The phase transition temperatures (° C.) observed with a microscope equipped with a hot stage were as follows:

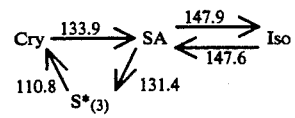

EXAMPLE 12

The liquid crystal compound, N-4-(1,1,1-trifluoro-2-octyloxycarbonyl)phenyl 4'-n-decyloxybiphenyl-4-carboxamide obtained in Example 3 was filled in the form of an isotropic phase to a liquid crystal cell having a cell thickness of 1.6 μm and having rubbed polyimide alignment films on ITO electrode substrates to prepare a liquid crystal thin film cell.

The liquid crystal cell thus prepared was arranged on a polarizing microscope equipped with a photomultiplier where two polarizing plates were orthogonally arranged with each other, in such a state that the visual field is dark when voltage is 0V.

Figure 5A:
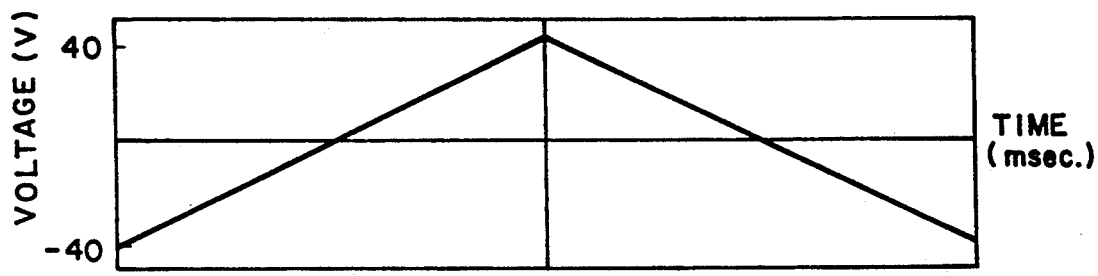
FIG. 5(a) shows a triangular wave applied.
Figure 5B:
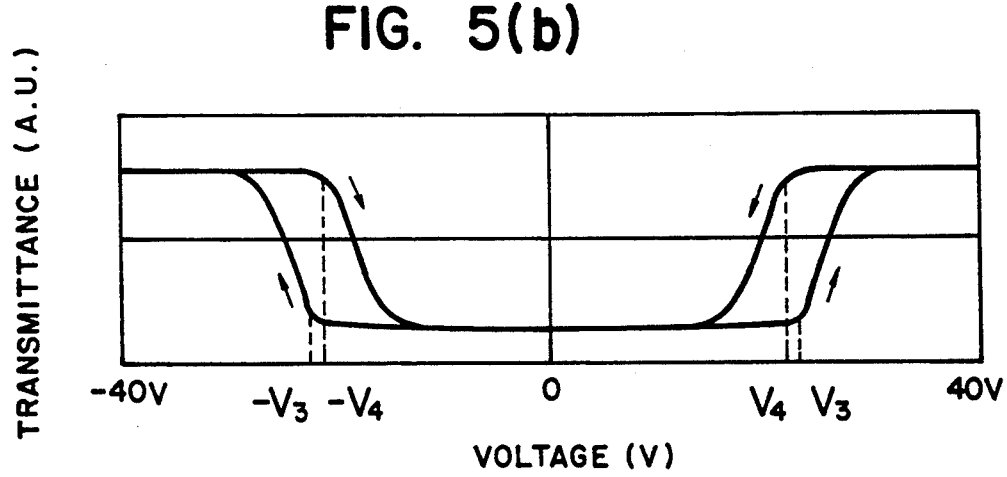
FIG. 5(b) a hysteresis of a liquid crystal cell.

The liquid crystal cell was slowly cooled down to the phase SA at a temperature gradient of 0.1 to 1.0° C./min. The cell was further cooled down and applied with a triangular wave voltage of ±40 volt and 1 Hz as shown in FIG. 5 (a) at a temperature within a range from 133.0° C. to 122.9° C. From the relationship between the applied voltage at a temperature of 128° C. and transmittance, the hysteresis curve as shown in FIG. 5 (b) was obtained.

The visual field kept a dark state from 0V to $+V_3$. It became a bright state after a steep rising at $+V_3$. When the applied voltage was changed toward the direction of minus (−), the visual field kept a bright state from +40V to $+V_4$, and it suddenly became a dark state at $+V_4$. The dark state was kept from 0V to $-V_3$, and became a bright after a steep rising at $-V_3$. The bright state was kept from −40V to $-V_4$, and suddenly became a dark state at $-V_4$. When the applied voltage was changed from +40V to −40V, it was observed that the visual field was changed in such three states as bright to dark to bright accompanied with the switching, and existence of three stable aligned states of liquid crystal molecules was confirmed.

The same effects were confirmed with the compounds of even other Examples in S*(3) phase.

We claim:

1. An antiferroelectric liquid crystal compound represented by the following formula:

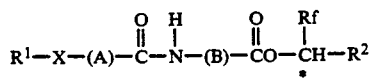

wherein $R^1$ and $R^2$ are independently selected from $C_3$-$C_{18}$ alkyl groups, respectively, Rf is a fluorinated lower alkyl group, X is —O— or —COO—, (A) and (B) are each independently selected from the group consisting of 1,4-phenylene and biphenylene which may be substituted with a halogen atom, and the C having an asterisk indicates an asymmetric carbon atom.

2. The antiferroelectric liquid crystal compound according to claim 1 wherein (A) is biphenylene and (B) is 1,4-phenylene.

3. The antiferroelectric liquid crystal compound according to claim 1 wherein X is carbonyloxy.

4. The antiferroelectric liquid crystal compound according to claim 1 wherein Rf is selected from the group consisting of —CF$_3$, —C$_2$F$_5$, —CHF$_2$, and —CH$_2$F.

5. The antiferroelectric liquid crystal compound according to claim 3 wherein the (A) is biphenylene and (B) is 1,4-phenylene.

6. An antiferroelectric liquid crystal compound represented by the formula:

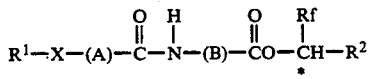

wherein $R^1$ and $R^2$ are indecently selected from $C_3$-$C_{18}$ alkyl groups, respectively, Rf is a fluorinated lower alkyl selected from the group consisting of —CF$_3$, —C$_2$F$_5$, —CHF$_2$, and —CH$_2$F, X is selected from the group consisting of —O— and —COO—, (A) and (B) are each independently selected from the group consisting of 1,4-phenylene and biphenylene.

* * * * *